(12) United States Patent
Vandenbossche et al.

(10) Patent No.: US 6,391,062 B1
(45) Date of Patent: May 21, 2002

(54) USE OF CATIONIC FUSED POLYCYCLIC COMPOUNDS FOR DYEING KERATIN SUBSTANCES, DYE COMPOSITIONS AND DYEING PROCESSES

(75) Inventors: Jean Jacques Vandenbossche, Tartas; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/500,522

(22) Filed: Feb. 9, 2000

(30) Foreign Application Priority Data

Feb. 9, 1999 (FR) .............................. 99 01504
Apr. 2, 1999 (FR) .............................. 99 04185

(51) Int. Cl.$^7$ ................................. A61K 7/13
(52) U.S. Cl. .................. 8/405; 8/407; 8/453; 8/461
(58) Field of Search ....................... 8/405, 407, 453, 8/461

(56) References Cited

U.S. PATENT DOCUMENTS 3,880,859 A  4/1975  Scheuermann et al. ..... 260/281
4,139,532 A  2/1979  Scheuermann et al. ....... 546/99
6,060,601 A  * 5/2000  Langhals et al. ............. 546/37

FOREIGN PATENT DOCUMENTS

DE  21 47 706  3/1973
FR  1 557 945  2/1969

OTHER PUBLICATIONS

English language Derwent Abstract of DE 21 47 706.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett, & Dunner, L.L.P.

(57) ABSTRACT

The invention relates to the use of fused polycyclic compounds having at least one cationic group Z, Z being chosen from quaternized aliphatic chains, aliphatic chains having at least one quaternized saturated ring and aliphatic chains having at least one quaternized unsaturated ring, as direct dyes in compositions intended for dyeing keratin substances and, in particular, compositions intended for dyeing human keratin fibers, especially the hair, and cosmetic compositions intended for making up the skin, the nails and the lips, to the dye compositions or make-up compositions containing them and to the direct dyeing process using them.

53 Claims, No Drawings

USE OF CATIONIC FUSED POLYCYCLIC COMPOUNDS FOR DYEING KERATIN SUBSTANCES, DYE COMPOSITIONS AND DYEING PROCESSES

This application claims priority to French patent application Nos. 99-01504, filed Feb. 9, 1999, and 99-04185, filed Apr. 2, 1999, the disclosures of both of which are incorporated by reference herein. The invention relates to compositions containing fused polycyclic compounds comprising at least one cationic group Z, Z being chosen from quaternized aliphatic chains, aliphatic chains comprising at least one quaternized saturated ring and aliphatic chains comprising at least one quaternized unsaturated ring. In particular, the invention relates to the use of such compounds as direct dyes in compositions for dyeing keratin substances and, preferably, compositions for dyeing human keratin fibers, especially the hair. The invention is also drawn to the use of such compounds in cosmetic compositions for making up the skin, the nails and the lips. Finally, the invention is drawn to dye compositions or make-up compositions containing the fused polycyclic compounds and to the corresponding direct dyeing process.

In the field of hair dyeing, direct dyes are sought, ie., dyes which, without supplying an oxidizing agent, are capable by themselves of temporarily modifying the natural shade of the hair. In this application, the dyes must satisfy a certain number of criteria, and, in particular, they must give rise to reproducible dyeing results with rich and varied shades allowing a wide range of colors to be obtained to be able to satisfy formulators, these dyeing results also needing to be intense and able to withstand washing, rubbing, permanent-waving, light and perspiration.

The inventors have now discovered, entirely surprisingly and unexpectedly, that fused polycyclic compounds of formula (I) defined below, comprising at least one cationic group Z, Z being chosen from quaternized aliphatic chains, aliphatic chains comprising at least one quaternized saturated ring and aliphatic chains comprising at least one quaternized unsaturated ring, are suitable for use as direct dyes for direct dyeing, and that they also make it possible to obtain dye compositions leading to intense and varied colorations that have excellent properties of resistance with respect to the various treatments to which keratin fibers may be subjected, and, in particular, with respect to light, washing, permanent-waving and perspiration. Finally, these compounds have better solubility in the media conventionally used for dyeing keratin fibers and are found to be easy to synthesize. These discoveries form the basis of the present invention.

Additional features and advantages of the invention are set forth in the description that follows, and, in part, will be apparent from the description or may be learned from practice of the invention. The advantages of the invention will be realized and attained by the compositions and processes particularly pointed out in the written description and claims. Both the foregoing general description and the following detailed description of the invention are exemplary and explanatory only and are not restrictive of the claimed invention.

A first subject of the invention is thus the use, as direct dyes in, or for the manufacture of, dye compositions for keratin substances, and, in particular, for human keratin fibers, such as the hair, of fused polycyclic compounds of formula (I) below, and the acid addition salts thereof:

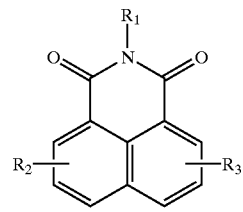

(I)

in which:

$R_1$ represents a hydrogen atom; a group Z defined below; an amino($C_1$–$C_6$)alkylcarbonyl ($C_1$–$C_6$)alkyl radical; an N—Z-amino($C_1$–$C_6$)alkylcarbonyl ($C_1$–$C_6$)alkyl radical; an N—($C_1$–$C_6$)alkylamino-($C_1$–$C_6$) alkylcarbonyl-($C_1$–$C_6$)alkyl radical; an N,N-di($C_1$–$C_6$) alkylamino-($C_1$–$C_6$)alkylcarbonyl($C_1$–$C_6$)alkyl radical; an amino-sulphonyl($C_1$–$C_6$)alkyl radical; an N—Z-aminosulphonyl-($C_1$–$C_6$)alkyl radical; an N—($C_1$–$C_6$)alkylaminosulphonyl-($C_1$–$C_6$)alkyl radical; an N,N-di($C_1$–$C_6$)alkylaminosulphonyl ($C_1$–$C_6$) alkyl radical; a carbamyl($C_1$–$C_6$)alkyl radical; an N—($C_1$–$C_6$)alkylcarbamyl ($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy-($C_1$–$C_6$)alkyl radical; a $C_1$–$C_6$ trifluoroalkyl radical;

$R_2$ and $R_3$, which may be identical or different, represent a hydrogen atom; a halogen atom; a group Z; a ($C_1$–$C_6$) alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino ($C_1$–$C_6$)alkylcarbonyl radical; an N,N-di($C_1$–$C_6$)alkylamino($C_1$–$C_6$) alkylcarbonyl radical; an amino($C_1$–$C_6$)alkylcarbonyl ($C_1$–$C_6$)alkyl radical; an N—Z-amino($C_1$–$C_6$) alkylcarbonyl ($C_1$–$C_6$)alkyl radical; an N—($C_1$–$C_6$) alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; a carboxyl radical; a ($C_1$–$C_6$) alkylcarboxy radical; a $C_1$–$C_6$ alkylsulphonyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; an aminosulphonyl($C_1$–$C_6$)alkyl radical; an N—Z-aminosulphonyl($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$) alkylcarbamyl radical; a carbamyl ($C_1$–$C_6$)alkyl radical; an N—($C_1$–$C_6$)- alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; an amino radical; an N—($C_1$–$C_6$)alkylamino radical; an N,N-di($C_1$–$C_6$) alkylamino radical (the two alkyl substituents possibly forming a 5- or 6-membered ring); an N-hydroxy ($C_1$–$C_6$)alkylamino radical; an N,N-bis(hydroxy ($C_1$–$C_6$)alkyl)amino radical; an N-polyhydroxy ($C_2$–$C_6$)alkylamino radical; an N,N-bis(polyhydroxy ($C_2$–$C_6$)alkyl)amino radical; an amino ($C_1$–$C_6$) alkylamino radical in which the terminal amino group is unsubstituted or substituted with one or two $C_1$–$C_6$ alkyl radicals, the alkyl radicals possibly forming a saturated or unsaturated 5- or 6-membered ring; an amino group protected with a $(C_1-C_6)$alkylcarbonyl, trifluoro$(C_1-C_6)$alkylcarbonyl, amino$(C_1-C_6)$ alkylcarbonyl, N—Z-amino$(C_1-C_6)$alkylcarbonyl, N—$(C_1-C_6)$alkylamino $(C_1-C_6)$alkylcarbonyl, N,N-di $(C_1-C_6)$alkylamino$(C_1-C_6)$alkylcarbonyl or formyl radical; a group $OR_4$ or $SR_4$;

$R_4$ denotes a $C_1-C_6$ alkyl radical; a $C_1-C_6$ monohydroxyalkyl radical; a $C_2-C_6$ polyhydroxyalkyl radical; a group Z; a $(C_1-C_6)$alkoxy$(C_1-C_6)$alkyl radical; an aryl radical; a carboxy$(C_1-C_6)$alkyl radical; a benzyl radical; a $(C_1-C_6)$alkylcarboxy$(C_1-C_6)$alkyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a $C_1-C_6$ trifluoroalkyl radical; a $C_1-C_6$ aminosulphonylalkyl radical; a $C_1-C_6$ N—Z-aminosulphonylalkyl radical; an N—$(C_1-C_6)$ alkylaminosulphonyl$(C_1-C_6)$alkyl radical; an N,N-di $(C_1-C_6)$alkylaminosulphonyl$(C_1-C_6)$alkyl radical; a $(C_1-C_6)$alkylsulphinyl $(C_1-C_6)$alkyl radical; a $(C_1-C_6)$ alkylsulphonyl$(C_1-C_6)$alkyl radical; a $(C_1-C_6)$ alkylcarbonyl $(C_1-C_6)$alkyl radical; a $C_1-C_6$ aminoalkyl radical; a $C_1-C_6$ aminoalkyl radical in which the amine is substituted with one or two identical or different radicals chosen from $C_1-C_6$ alkyl, $C_1-C_6$ monohydroxyalkyl, $C_2-C_6$ polyhydroxyalkyl, $(C_1-C_6)$ alkylcarbonyl, formyl, trifluoro$(C_1-C_6)$alkylcarbonyl, $(C_1-C_6)$alkylcarboxyl and $C_1-C_6$ alkylsulphonyl radicals.

The substituents $R_2$ and $R_3$ can together form an unsaturated ring of structure (II) below:

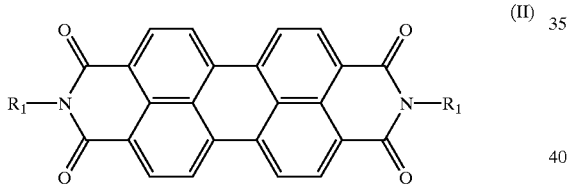

(II)

Z is chosen from the unsaturated cationic groups of formulae (III) and (IV) below, and the saturated cationic groups of formula (V) below:

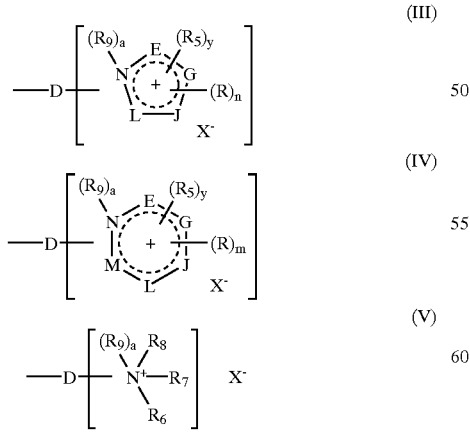

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1-C_6$ alkoxy radicals, and which can bear one or more ketone functions;

the ring members E, G, J, L and M, which may be identical or different, represent a carbon, oxygen, sulphur or nitrogen atom;

n is an integer ranging from 0 to 4 inclusive;

m is an integer ranging from 0 to 5 inclusive;

the radicals R, which may be identical or different, represent a covalent bond; a group Z, a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a cyano $(C_1-C_6)$ alkyl radical, a $C_1-C_6$ alkoxy radical, a tri$(C_1-C_6)$ alkylsilane$(C_1-C_6)$alkyl radical, an amido radical, an aldehydo radical, a carboxyl radical, a $(C_1-C_6)$ alkylcarbonyl radical, a thio radical, a $C_1-C_6$ thioalkyl radical, a $C_1-C_6$ alkylthio radical, an amino radical, an amino radical protected with a $(C_1-C_6)$alkylcarbonyl, carbamyl or $C_1-C_6$ alkylsulphonyl radical; a group NHR" or NR"R'" in which R" and R'", which may be identical or different, represent a $C_1-C_6$ alkyl radical, a $C_1-C_6$ monohydroxyalkyl radical or a $C_2-C_6$ polyhydroxyalkyl radical;

when, in formula (III) or (IV), n or m is greater than 2, two adjacent radicals R can together also form an unsaturated 5- or 6-membered ring which is carbon-based or which contains one or more hetero atoms; examples of the heterocycles include pyrazolotriazolinium, pyrazoloimidazolinium, pyrrolotriazolinium, pyrazolopyrimidinium, pyrazolopyridinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyridinium groups;

$R_5$ represents a covalent bond, a $C_1-C_6$ alkyl radical, a $C_1-C_6$ monohydroxyalkyl radical, a $C_2-C_6$ polyhydroxyalkyl radical, a cyano$(C_1-C_6)$alkyl radical, a tri $(C_1-C_6)$alkylsilane $(C_1-C_6)$alkyl radical, a $(C_1-C_6)$ alkoxy$(C_1-C_6)$alkyl radical, a carbamyl-$(C_1-C_6)$alkyl radical, a $(C_1-C_6)$alkylcarboxy$(C_1-C_6)$-alkyl radical, a benzyl radical or a group Z;

$R_6$, $R_7$ and $R_8$, which may be identical or different, represent a covalent bond, a $C_1-C_6$ alkyl radical, a $C_1-C_6$ monohydroxyalkyl radical, a $C_2-C_6$ polyhydroxyalkyl radical, a $(C_1-C_6)$alkoxy$(C_1-C_6)$alkyl radical, a cyano$(C_1-C_6)$alkyl radical, an aryl radical, a benzyl radical, a $C_1-C_6$ amidoalkyl radical, a tri $(C_1-C_6)$alkylsilane$(C_1-C_6)$alkyl radical or a $C_1-C_6$ aminoalkyl radical in which the amine is protected with a $(C_1-C_6)$alkylcarbonyl, carbamyl or $C_1-C_6$ alkylsulphonyl radical; two of the radicals $R_6$, $R_7$ and $R_8$ can together also form, with the nitrogen atom to which they are attached, a saturated 5- or 6-membered ring which is carbon-based or which contains one or more hetero atoms such as, for example, a pyrrolidine ring, a piperidine ring, a piperazine ring or a morpholine ring, it being possible for the ring to be unsubstituted or substituted with a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a cyano$(C_1-C_6)$alkyl radical, a $C_1-C_6$ alkoxy radical, a tri$(C_1-C_6)$alkylsilane$(C_1-C_6)$ alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$alkylthio radical, an amino radical or an amino radical protected with a ($C_1$–$C_6$)alkylcarbonyl, carbamyl or $C_1$–$C_6$ alkylsulphonyl radical;

one of the radicals $R_6$, $R_7$ and $R_8$ can also represent a second group Z which is identical to or different from the first group Z;

$R_9$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl ($C_1$–$C_6$)alkyl radical; a $C_1$–$C_6$ trifluoroalkyl radical; a tri ($C_1$–$C_6$)alkylsilane-($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

a and y are integers equal to 0 or 1; with the following conditions:

in the unsaturated cationic groups of formula (III):
when a=0, the linker arm D is attached to the nitrogen atom,
when a=1, the linker arm D is attached to one of the ring members E, G, J or L,
y can take the value 1 only:
1) when the ring members E, G, J and L simultaneously represent a carbon atom and when the radical $R_5$ is borne by the nitrogen atom of the unsaturated ring; or, alternatively,
2) when at least one of the ring members E, G, J and L represents a nitrogen atom to which the radical $R_5$ is attached;

in the unsaturated cationic groups of formula (IV):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the radical $R_5$ is borne by the nitrogen atom of the unsaturated ring;

in the cationic groups of formula (V):
when a=0, then the linker arm D is attached to the nitrogen atom bearing the radicals $R_7$ and $R_8$,
when a=1, then two of the radicals $R_7$ and $R_8$ form, together with the nitrogen atom to which they are attached, a saturated 5- or 6-membered ring as defined above, and the linker arm D is borne by a carbon atom of the saturated ring;

$X^-$ represents a monovalent or divalent anion, and is preferably chosen from a halogen atom, such as chlorine, bromine, fluorine or iodine, a hydroxide, a hydrogen sulphate or a $C_1$–$C_6$ alkyl sulphate such as, for example, a methyl sulphate or an ethyl sulphate;

it being understood that:
the number of cationic groups Z of formulae (III), (IV) or (V) is at least equal to 1.

In the formulae (I), (II), (III), (IV) and (V) above, the alkyl and alkoxy radicals can be linear or branched. The compounds of formula (I) can optionally be salified with strong inorganic acids such as HCl, HBr or $H_2SO_4$, or organic acids such as acetic acid, tartaric acid, lactic acid, citric acid or succinic acid. Among the rings of the unsaturated groups Z of formula (III) above, particular examples include pyrrole, imidazole, pyrazole, oxazole, thiazole and triazole rings. Among the rings of the unsaturated groups Z of formula (IV) above, particular examples include pyridine, pyrimidine, pyrazine, oxazine and triazine rings.

Among the compounds of formulae (I) and (II) above, particular compounds include:

N,N'-dihexyl-1,3,8,10-tetrahydro-N,N,N',N'-tetramethyl-1, 3,8,10-tetraoxoanthra{2,1,9-def:6,5,10-d'e'f'}diisoquinoline-2,9-dipropanaminium diiodide; 4,4'-{(1,3,8,10-tetrahydro-1,3,8,10-tetraoxoanthra-{2,1,9-def:6,5,10-d'e'f'}diisoquinoline-2,9-diyl)di-3,1-propanediyl}bis{4-methyl}morpholinium diiodide;

N,N,N',N'-tetraethyl-1,3,8,10-tetrahydro-N,N'-dimethyl-1, 3,8,10-tetraoxoanthra{2,1,9-def:6,5,10-d'e'f'}diisoquinoline-2,9-dipropanaminium diiodide; N,N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium diiodide;

N,N'-diethyl-1,3,8,10-tetrahydro-N,N,N',N'-tetramethyl-1, 3,8,10-tetraoxoanthra{2,1,9-def:6,5,10-d'e'f'}diisoquinoline-2,9-dipropanaminium diiodide; 1,3, 8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-dipropanaminium diiodide;

N,N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium dibenzenesulphonate;

1,3,8,10-tetrahydro-N,N,N,N',N',N'-hexaethyl-1,3,8,10-tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium dibenzenesulphonate;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

bis{1,1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8 ,10-tetraoxoanthra{2,1,9-def:6,5,10-d'e'f'}diisoquinoline-2,9-diyl)di-3,1 -propanediyl}imidazolinium dimethosulphate.

Among these compounds of formula (I) or (II), the following are more particularly preferred:

1,3,8,10-tetrahydro-N,N,N,N',N',N'-hexamethyl-1,3,8,10-tetraoxoanthra{2,1,9-def:6,5,10-d'e'f'}diisoquinoline-2,9-dipropanaminium diiodide;

bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8,10-tetraoxoanthra(2,1,9-def:6,5,10-d'e'f'}diisoquinoline-2,9-diyl)di-3,1-propanediyl}imidazolinium dimethosulphate.

The compounds of formula (I) or (II) according to the invention can be readily obtained according to methods that are well known in the state of the art for the production of quaternized amines, for example:

in a single stage, by coupling a compound comprising a haloalkyl radical with a compound bearing a tertiary amine radical, or by coupling a compound comprising a tertiary amine radical with a compound bearing a haloalkyl radical;

or, in two stages, by coupling a compound comprising a haloalkyl radical with a compound bearing a secondary amine, or by coupling an anhydride with an amino (disubstituted)alkylamine (scheme below), followed by quaternization with an alkylating agent.

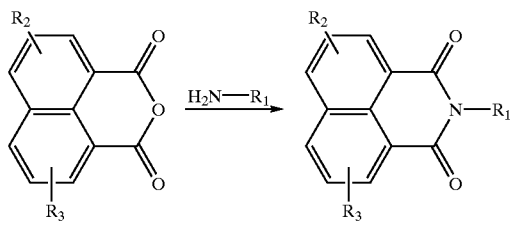

The quaternization step is generally, for convenience, the final step of the synthesis, but may be performed earlier in the sequence of reactions leading to the preparation of the compounds of formula (I) or (II).

Another subject of the invention is a composition for dyeing or making up keratin fibers, comprising, in a medium suitable for dyeing or for make-up, an effective amount of at least one compound of formula (I) in accordance with the invention. For the purposes of the present invention, the expression "keratin substances" refers mainly to the skin of the face or the body, the lips, the nails, human keratin fibers, such as human head hair, body hair, the eyelashes, the eyebrows and also keratin fibers, such as natural textile fibers, especially wool.

A subject of the invention is, in particular, a composition for the direct dyeing of human keratin fibers such as the hair, comprising, in a medium suitable for dyeing, an effective amount of at least one compound of formula (I) in accordance with the invention. When the composition is intended for dyeing, the cationic fused polycyclic compound(s) of formula (I) in accordance with the invention, and/or the acid addition salt(s) thereof, preferably represent(s) from 0.005 to 12% by weight approximately relative to the total weight of the dye composition, and even more preferably from 0.05 to 6% by weight approximately relative to this weight. When the composition is intended for make-up, the cationic fused polycyclic compound(s) of formula (I) in accordance with the invention, and/or the acid addition salt(s) thereof, preferably represent(s) from 0.005 to 25% by weight approximately relative to the total weight of the composition, and even more preferably from 0.05 to 15% by weight approximately relative to this weight.

The compounds of formula (I) in accordance with the invention can also be used in well-known processes of oxidation dyeing of human keratin fibers, using oxidation dyes (oxidation dye precursors and optionally couplers), to vary the shade of the dyeing results obtained with the oxidation dyes, or to enrich them with glints.

Besides the cationic fused polycyclic compounds of formula (I) according to the invention, the dye composition according to the invention can also contain, to broaden the range of shades and to obtain varied shades, other direct dyes conventionally used, and, in particular, nitrobenzene dyes, such as nitrophenylenediamines, nitrodiphenylamines, nitroanilines, nitrophenyl ethers or nitrophenols, and nitropyridines, anthraquinone dyes, mono- or diazo dyes, triarylmethane dyes, azine dyes, acridine dyes and xanthene dyes, or, alternatively, metalliferous dyes. The proportion of all these other direct addition dyes can range from 0.5 to 10% by weight approximately relative to the total weight of the dye composition.

The medium suitable for dyeing (or the support) generally comprises water or a mixture of water and at least one organic solvent to dissolve the compounds not sufficiently soluble in water. As organic solvent, examples include $C_1$–$C_4$ lower alkanols, such as ethanol and isopropanol; glycerol; glycols and glycol ethers such as 2-butoxyethanol, propylene glycol, propylene glycol monomethyl ether, as well as aromatic alcohols such as benzyl alcohol or phenoxyethanol, similar products and mixtures thereof. It may also contain fatty substances, such as oils and waxes. The solvents can be present in proportions preferably ranging from 1 to 40% by weight approximately relative to the total weight of the dye composition, and even more preferably from 5 to 30% by weight approximately.

Fatty amides such as mono- and diethanolamides of acids derived from coconut, from lauric acid or from oleic acid can also be added to the composition according to the invention, in concentrations ranging from about 0.05 to 10% by weight. Surfactants that are well known in the state of the art and of anionic, cationic, nonionic, amphoteric or zwitterionic type or mixtures thereof can also be added to the composition according to the invention, preferably in a proportion ranging from about 0.1 to 50% by weight, and advantageously from about 1 to 20% by weight relative to the total weight of the composition. Thickeners can also be used, in a proportion ranging from about 0.2 to 5%. The dye composition can also contain various common adjuvants, such as antioxidants, fragrances, sequestering agents, dispersants, hair conditioners, preserving agents and opacifiers, as well as any other adjuvant usually used in the dyeing of keratin fibers. Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The pH of the dye composition according to the invention intended for the dyeing of keratin fibers generally ranges from 3 to 12 approximately, and preferably from 5 to 11 approximately. It can be adjusted to the desired value using acidifying or basifying agents commonly used to dye keratin fibers. Examples of acidifying agents include inorganic or organic acids such as hydrochloric acid, orthophosphoric acid, sulphuric acid, carboxylic acids such as acetic acid, tartaric acid, citric acid and lactic acid, and sulphonic acids. Examples of basifying agents include aqueous ammonia, alkaline carbonates, alkanolamines, such as mono-, di- and triethanolamine and derivatives thereof, sodium hydroxide, potassium hydroxide and the compounds of formula (VI) below:

in which W is a propylene residue optionally substituted with a hydroxyl group or a $C_1$–$C_6$ alkyl radical; $R_{10}$, $R_{11}$, $R_{12}$ and $R_{13}$, which are identical or different, represent a hydrogen atom, a $C_1$–$C_6$ alkyl radical or a $C_1$–$C_6$ hydroxyalkyl radical.

The dye composition according to the invention can be in various forms, such as in the form of liquids, creams, gels or poultices, or any other form suitable for dyeing keratin substances, especially human hair. In particular, it can be packaged under pressure in an aerosol can in the presence of a propellant and can form a mousse. The cosmetic compositions intended for make-up use are, in particular,

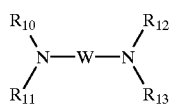

(VI)

make-up products for the face or the lips, such as eyeshadows, face powders, rouges and blushers, foundations, lipsticks or lip glosses and make-up products for the human body; they are also make-up products for the eyelashes, for the eyebrows and for the nails, such as mascaras, eyebrow pencils, eyeliners and nail varnishes.

Another subject of the invention relates to a process for dyeing keratin fibers, and, in particular, human keratin fibers, such as the hair, by direct dyeing, which comprises leaving a composition containing at least one cationic fused polycyclic compound of formula (I) to act on wet or dry keratin fibers. The composition according to the invention can be used as a leave-in composition, i.e., after the composition has been applied to the fibers, they are dried without intermediate rinsing. In the other modes of application, after the composition has been applied to the fibers for an exposure time ranging from 3 to 60 minutes approximately, preferably from 5 to 45 minutes approximately, the fibers are rinsed, optionally washed, and then rinsed again and dried.

The present invention is further illustrated by the following examples which are designed to teach those of ordinary skill in the art how to practice the invention. The following examples are merely illustrative of the invention and should not be construed as limiting the invention as claimed.

EXAMPLES OF DYE COMPOSITIONS

Examples 1 and 2

The 2 direct dye compositions for hair given in the table below were prepared (all contents expressed in grams - A.M. denotes active material):

|  | Example 1 | Example 2 |
|---|---|---|
| Dye of formula (I) 1* | 0.890 |  |
| Dye of formula (I) 2** |  | 0.859 |
| Benzyl alcohol | 10 | 10 |
| Ethanol | 21 | 21 |
| Buffer pH 7 qs | pH 7 | pH 7 |
| Demineralized water | 100 | 100 |

*bis{1-1'-methyl}-1,1'-{(1,3,8,10-tetrahydro-1,3,8,10-tetraoxanthra{2,1,9-def:6,5,10-d'e'f'}diisoquinoline-2,9-diyl)di-3,1-propanediyl}imidazolinium diiodide;
**bis{1-1'-methyl}-1,1'-{(1,3,8,10-tetrahydro-1,3,8,10-tetraoxanthra{2,1,9-def:6,5,10-d'e'f'}diisoquinoline-2,9-diyl)di-3,1-propanediyl}imidazolinium dimethosulphate.

Each of the above compositions was applied to locks of natural or permanent-waved grey hair containing 90% white hairs and was left for an exposure time of 20 minutes. After rinsing with running water and drying, the hair was dyed in a shade given in the table below.

| Composition of Example 1 | iridescent red |
|---|---|
| Composition of Example 2 | iridescent red |

EXAMPLES OF MAKE-UP COMPOSITIONS

Example 3

Lipstick

| Polyethylene wax | 14 g |
|---|---|
| Sesame oil | 78 g |
| Dye of formula (I) 1*defined in Example 1 | 5 g |
| Titanium dioxide | 3 g |

Procedure:

homogenized the oil+dye and pigment mixture for 45 minutes in an oil bath, 3 successive passages through a three-roll mill, homogenized the oil+dye and pigment mixture for 30 minutes in an oil bath, molded in a mold at 42° C. and 30 minutes in a freezer. A lipstick of an intense red was obtained.

Example 4

Blusher:

| Talc | 38 g |
|---|---|
| Mica | 20 g |
| Bismuth oxychoride | 8 g |
| Zinc stearate | 3 g |
| Nylon powder | 20 g |
| Dye of formula (I) 2**defined in Example 2 | 5 g |
| Fatty binder (*) qs | 100 g |

(*) Mixture of carbon-based oils which comprised:
3.6 g of capric/caprylic acid triglycerides,
2.0 g of hydrogenated isoparaffin (non-volatile),
1.0 g of jojoba oil.

Procedure:

Premixed all the fillers and dye and pigments, 5 minutes in a Lödige mixer (mixer for homogenizing powders), Added the organic binder, 5 minutes in a Lödige mixer, Treated with a jet of air (Chrispro), Screened at 160 microns.

Example 5

Foundation of oil-in-water type

| Phase A | |
|---|---|
| Stearic acid | 2.0% |
| Glyceryl stearate | 3.0% |
| Glyceryl isostearate | 2.0% |
| Mineral oil | 8.0% |
| Pigments | |
| Red iron oxide | 0.9% |
| Black iron oxide | 0.3% |
| Titanium dioxide | 4.4% |
| Dye of formula (I) 1*defined in Example 1 | 0.7% |
| Preserving agent | 0.2% |
| Dimethicone (5 cst) | 4.0% |
| Phase B | |
| Triethanolamine | 1.0% |

-continued

| Phase C | |
|---|---|
| Preserving agent | 0.2% |
| Magnesium aluminium silicate as a gel containing 5% active material | 20.0% |
| Cellulose gum | 3.5% |
| Sodium lauroyl sarcosinate | 3.5% |
| Glycerol | 2.0% |
| Water qs | 100% |
| Phase D | |
| Preserving agent | 0.3% |
| Water | 2.0% |

Procedure:

Phases A and C were prepared separately, they were heated to 80° C. and were then homogenized in a homogenizer sold under the name Moritz. Phase B was introduced into phase A and this mixture was then poured into phase C with stirring. Phase D was then added and stirring was continued until the mixture was completely cold. A beige-coloured foundation was obtained.

The foregoing written description relates to various embodiments of the present invention. Numerous changes and modifications may be made therein without departing from the spirit and scope of the invention as defined in the following claims.

What is claimed is:

1. A method of dyeing keratin substances, comprising applying to said keratin substances a direct dye composition comprising, in an amount effective for dyeing, at least one compound of formula (I) or an acid addition salt thereof:

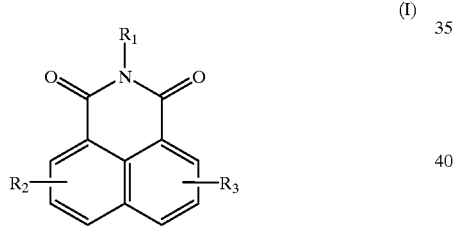

(I)

in which:
  $R_1$ is chosen from a hydrogen atom; a group Z; an amino($C_1$-$C_6$)alkylcarbonyl ($C_1$-$C_6$)alkyl radical; an N—Z-amino($C_1$-$C_6$)alkylcarbonyl($C_1$-$C_6$)alkyl radical; an N—($C_1$-$C_6$)alkylamino($C_1$-$C_6$)alkylcarbonyl ($C_1$-$C_6$)alkyl radical; an N,N-di($C_1$-$C_6$)alkylamino ($C_1$-$C_6$)alkylcarbonyl($C_1$-$C_6$)alkyl radical; an aminosulphonyl($C_1$-$C_6$)alkyl radical; an N—Z-aminosulphonyl($C_1$-$C_6$)alkyl radical; an N—($C_1$-$C_6$) alkylaminosulphonyl($C_1$-$C_6$)alkyl radical; an N,N-di ($C_1$-$C_6$)alkylamino-sulphonyl($C_1$-$C_6$)alkyl radical; a carbamyl($C_1$-$C_6$)alkyl radical; an N—($C_1$-$C_6$) alkylcarbamyl($C_1$-$C_6$)alkyl radical; an N,N-di($C_1$-$C_6$) alkylcarbamyl($C_1$-$C_6$)alkyl radical; a $C_1$-$C_6$ alkyl radical; a $C_1$-$C_6$ monohydroxyalkyl radical; a $C_2$-$C_6$ polyhydroxyalkyl radical; a ($C_1$-$C_6$)alkoxy($C_1$-$C_6$) alkyl radical; and a $C_1$-$C_6$ trifluoroalkyl radical;

$R_2$ and $R_3$, which are identical or different, are chosen from a hydrogen atom; a halogen atom; a group Z; a ($C_1$-$C_6$)alkylcarbonyl radical; an amino ($C_1$-$C_6$) alkylcarbonyl radical; an N—Z-amino($C_1$-$C_6$) alkylcarbonyl radical; an N—($C_1$-$C_6$)alkylamino($C_1$-$C_6$)alkylcarbonyl radical; an N,N-di($C_1$-$C_6$)alkylamino($C_1$-$C_6$) alkylcarbonyl radical; an amino($C_1$-$C_6$)alkylcarbonyl ($C_1$-$C_6$)alkyl radical; an N—Z-amino($C_1$-$C_6$) alkylcarbonyl($C_1$-$C_6$)alkyl radical; an N—($C_1$-$C_6$) alkylamino($C_1$-$C_6$)alkylcarbonyl($C_1$-$C_6$)alkyl radical; an N,N-di($C_1$-$C_6$)alkylamino($C_1$-$C_6$)alkylcarbonyl ($C_1$-$C_6$)alkyl radical; a carboxyl radical; a ($C_1$-$C_6$) alkylcarboxy radical; a $C_1$-$C_6$ alkylsulphonyl radical; an aminosulphonyl radical; an N—Z-aminosulphonyl radical; an N—($C_1$-$C_6$)alkylaminosulphonyl radical; an N,N-di($C_1$-$C_6$)alkylaminosulphonyl radical; an aminosulphonyl($C_1$-$C_6$)alkyl radical; an N—Z-aminosulphonyl($C_1$-$C_6$)alkyl radical; an N—($C_1$-$C_6$) alkylaminosulphonyl($C_1$-$C_6$)alkyl radical; an N,N-di ($C_1$-$C_6$)alkylaminosulphonyl($C_1$-$C_6$)alkyl radical; a carbamyl radical; an N—($C_1$-$C_6$)alkylcarbamyl radical; an N,N-di($C_1$-$C_6$)alkylcarbamyl radical; a carbamyl($C_1$-$C_6$)alkyl radical; an N—($C_1$-$C_6$) alkylcarbamyl($C_1$-$C_6$)alkyl radical; an N,N-di($C_1$-$C_6$) alkylcarbamyl($C_1$-$C_6$)alkyl radical; a $C_1$-$C_6$alkyl radical; a hydroxyl radical; a nitro radical; a $C_1$-$C_6$ monohydroxyalkyl radical; a $C_2$-$C_6$ polyhydroxyalkyl radical; a ($C_1$-$C_6$)alkoxy($C_1$-$C_6$)alkyl radical; a $C_1$-$C_6$ trifluoroalkyl radical; a cyano radical; an amino radical; an N—($C_1$-$C_6$)alkylamino radical; an N,N-di($C_1$-$C_6$) alkylamino radical, wherein the two alkyl substituents optionally form a 5- or 6-membered ring; an N-hydroxy ($C_1$-$C_6$) alkylamino radical; an N,N-bis(hydroxy ($C_1$-$C_6$)alkyl)amino radical; an N-polyhydroxy ($C_2$-$C_6$)alkylamino radical; an N,N-bis(polyhydroxy ($C_2$-$C_6$)alkyl)amino radical; an amino($C_1$-$C_6$) alkylamino radical in which the terminal amino group is unsubstituted or substituted with one or two $C_1$-$C_6$ alkyl radicals, said alkyl radicals optionally forming a saturated or unsaturated 5- or 6-membered ring; an amino group protected with a ($C_1$-$C_6$)alkylcarbonyl, trifluoro($C_1$-$C_6$)alkylcarbonyl, amino($C_1$-$C_6$) alkylcarbonyl, N—Z-amino($C_1$-$C_6$)alkylcarbonyl, N—($C_1$-$C_6$)alkylamino($C_1$-$C_6$)alkyl-carbonyl, N,N-di ($C_1$-$C_6$)alkylamino($C_1$-$C_6$)alkylcarbonyl or formyl radical; and a group $OR_4$ or $SR_4$;

$R_2$ and $R_3$ alternatively may together form an unsaturated ring of formula (II) below:

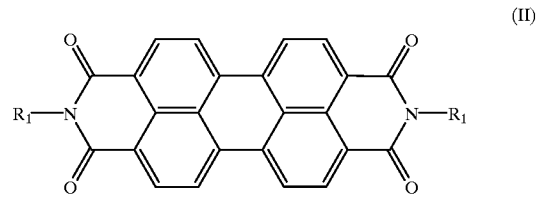

(II)

in which said radical $R_1$ is chosen from a hydrogen atom; a group Z; an amino($C_1$-$C_6$)alkylcarbonyl ($C_1$-$C_6$)alkyl radical; an N—Z-amino($C_1$-$C_6$) alkylcarbonyl($C_1$-$C_6$)alkyl radical; an N—($C_1$-$C_6$) alkylamino($C_1$-$C_6$)alkyl carbonyl($C_1$-$C_6$)alkyl radical; an N,N-di($C_1$-$C_6$)alkylamino($C_1$-$C_6$)alkylcarbonyl ($C_1$-$C_6$)alkyl radical; an amino-sulphonyl($C_1$-$C_6$)alkyl radical; an N—Z-aminosulphonyl($C_1$-$C_6$)alkyl radical; an N—($C_1$-$C_6$)alkylaminosulphonyl($C_1$-$C_6$)alkyl radical; an N,N-di($C_1$-$C_6$)alkylamino-sulphonyl($C_1$-$C_6$) alkyl radical; a carbamyl($C_1$-$C_6$)alkyl radical; an N—($C_1$-$C_6$)alkylcarbamyl($C_1$-$C_6$)alkyl radical; an N,N-di($C_1$-$C_6$)alkylcarbamyl($C_1$-$C_6$)alkyl radical; a $C_1$-$C_6$ alkyl radical; a $C_1$-$C_6$ monohydroxyalkyl radical; a $C_2$-$C_6$ polyhydroxyalkyl radical; a ($C_1$-$C_6$) alkoxy($C_1$-$C_6$)alkyl radical; and a $C_1$-$C_6$ trifluoroalkyl radical;

$R_4$ is chosen from a $C_1$–$C_6$ alkyl radical; a $C_1$–$C_6$ monohydroxyalkyl radical; a $C_2$–$C_6$ polyhydroxyalkyl radical; a group Z; a ($C_1$–$C_6$)alkoxy($C_1$–$C_6$)alkyl; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl ($C_1$–$C_6$)alkyl radical; an N—($C_1$–$C_6$)alkyl-carbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonyl-alkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; a $C_1$–$C_6$ aminoalkyl radical; and a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro ($C_1$–$C_6$)alkylcarbonyl, ($C_1$–$C_6$) alkylcarboxyl, and $C_1$–$C_6$ alkylsulphonyl radicals;

Z is chosen from an unsaturated cationic group of formulae (III) or (IV), and a saturated cationic group of formula (V):

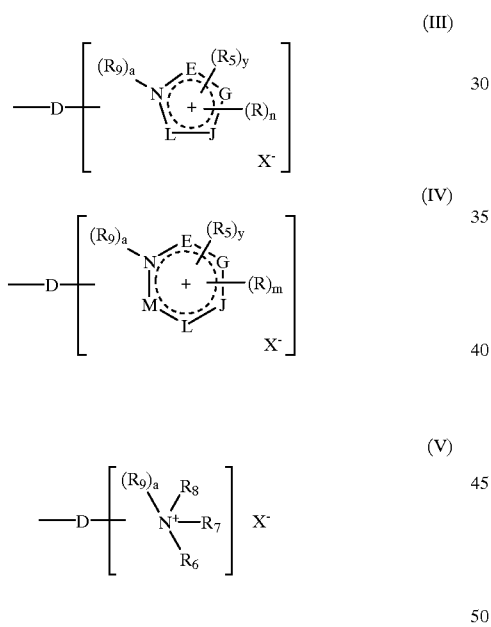

in which:

D is a linker arm chosen from linear and branched alkyl chains, said chains being optionally interrupted by one or more hetero atoms, optionally substituted with one or more hydroxyl or $C_1$–$C_6$ alkoxy radicals, and optionally having one or more ketone functions;

$X^-$ is chosen from monovalent and divalent anions;

said ring members E, G, J, L and M, which are identical or different, are chosen from a carbon, oxygen, sulphur or nitrogen atom;

n is an integer ranging from 0 to 4;

m is an integer ranging from 0 to 5;

said radicals R, which are identical or different, are chosen from a covalent bond, a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; and a group NHR" or NR"R'" in which R" and R'", which are identical or different, and are chosen from a $C_1$–$C_6$ alkyl radical, a $C_1$–$C_6$ monohydroxyalkyl radical and a $C_2$–$C_6$ polyhydroxyalkyl radical; when, in formula (III) or (IV), n or m is greater than 2, two adjacent radicals R together optionally form an unsaturated 5- or 6-membered ring which is carbon-based or which contains one or more hetero atoms;

$R_5$ is chosen from a covalent bond, a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane ($C_1$–$C_6$)alkyl radical, a ($C_1$–$C_6$)alkoxy($C_1$–$C_6$)alkyl radical, a carbamyl-($C_1$–$C_6$)alkyl radical, a ($C_1$–$C_6$)alkylcarboxy ($C_1$–$C_6$)alkyl radical, a benzyl radical and a group Z;

$R_6$, $R_7$ and $R_8$, which are identical or different, are chosen from a covalent bond, a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$)alkyl radical, an aryl radical, a benzyl radical, a $C_1$–$C_6$ amidoalkyl radical, a tri($C_1$–$C_6$)alkylsilane($C_1$–$C_6$)alkyl radical and a $C_1$–$C_6$ aminoalkyl radical in which the amine is protected with a ($C_1$–$C_6$)alkylcarbonyl, carbamyl or $C_1$–$C_6$ alkylsulphonyl radical; two of the radicals $R_6$, $R_7$ and $R_8$ together optionally form, with the nitrogen atom to which they are attached, a saturated 5- or 6-membered ring which is carbon-based or contains one or more hetero atoms, one of the radicals $R_6$, $R_7$ and $R_8$ optionally is chosen from a second group Z which is identical to or different from the first group Z;

$R_9$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl($C_1$–$C_6$)alkyl radical; a $C_1$–$C_6$ trifluoroalkyl radical; a tri($C_1$–$C_6$)alkylsilane-($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; and an N—($C_1$–$C_6$)alkylsulphonamido($C_1$–$C_6$)alkyl radical;

a and y are integers equal to 0 or 1; with the following provisos:

(A) in the unsaturated cationic groups of formula (III):

when a=0, the linker arm D is attached to the nitrogen atom, when a=1, the linker arm D is attached to one of the ring members E, G, J or L, y can take the value 1 only when:

(1) the ring-members E, G, J and L simultaneously are a carbon atom and when the radical R₅ is borne by the nitrogen atom of the unsaturated ring; or
(2) at least one of the ring members E, G, J and L is a nitrogen atom to which the radical R₅ is attached;
(B) in the unsaturated cationic groups of formula (IV):
when a=0, the linker arm D is attached to the nitrogen atom,
when a=1, the linker arm D is attached to one of the ring members E, G, J, L or M,
y can take the value 1 only when at least one of the ring members E, G, J, L and M is a divalent atom and when the radical R₅ is borne by the nitrogen atom of the unsaturated ring;
(C) in the cationic groups of formula (V):
when a=0, then the linker arm D is attached to the nitrogen atom bearing the radicals R₇ and R₈,
when a=1, then two of the radicals R₇ and R₈ form, together with the nitrogen atom to which they are attached, a saturated 5- or 6-membered ring as defined above, and the linker arm D is borne by a carbon atom of the saturated ring;
and with the overall proviso that:
the number of cationic groups Z of formula (III), (IV) or (V) is at least equal to 1.

2. A method according to claim 1, wherein said alkyl chain of said linker arm D contains from 1 to 14 carbon atoms.

3. A method according to claim 1, wherein said one or more heteroatoms optionally interrupting said alkyl chain of said linker arm D are chosen from oxygen, sulfur and nitrogen atoms.

4. A method according to claim 1, wherein said keratin substances are chosen from human skin, lips and nails.

5. A method according to claim 1, wherein said keratin substances are human keratin fibers.

6. A method according to claim 5, wherein said human keratin fibers are chosen from at least one of head hair, body hair, eyelashes and eyebrows.

7. A method according to claim 1, wherein said rings of the unsaturated groups Z of formula (III) are chosen from pyrrole, imidazole, pyrazole, oxazole, thiazole and triazole rings.

8. A method according to claim 1, wherein said rings of the unsaturated groups Z of formula (IV) are chosen from pyridine, pyrimidine, pyrazine, oxazine and triazine rings.

9. A method according to claim 1, wherein in said formula (V), two of the radicals R₆, R₇ and R₈ form a pyrrolidine ring, a piperidine ring, a piperazine ring or a morpholine ring, and said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$) alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical.

10. A method according to claim 1, wherein said anion X⁻ is chosen from a halogen atom, a hydroxide, a hydrogen sulphate and a ($C_1$–$C_6$)alkyl sulphate.

11. A method according to claim 1, wherein in said formula (I), R₂ and R₃ together form an unsaturated ring of formula (II).

12. A method according to claim 1, wherein said compounds of formula (I) are chosen from:

N,N'-dihexyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;

4,4'-{(1,3,8,10-tetrahydro-1,3,8,10-tetraoxoanthra-{2,1,9-def:6,5,10-d'e'f'}diisoquinoline-2,9-diyl)di-3,1-propanediyl}bis{4-methyl}morpholinium diiodide;

N,N,N',N'-tetraethyl-1,3,8,10-tetrahydro-N,N'-dimethyl-1,3,8,10-tetraoxoanthra{2,1,9-def:6,5,10-d'e'f'}diisoquinoine-2,9-dipropanaminium diiodide;

N,N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium diiodide;

N,N'-diethyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-dipropanaminium diiodide;

N,N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium dibenzenesulphonate;

1,3,8,10tetrahydro-N,N,N,N',N',N'-hexaethyl-1,3,8,10tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium dibenzenesulphonate;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosulphate.

13. A method according to claim 12, wherein said compounds of formula (I) are chosen from:

1,3,8,10-tetrahydro-N,N,N,N',N', N'-hexamethyl-1,3,8,10-tetraoxoanthra{2,1,9-def:6,5,10-d'e'f'}diisoquinoline-2,9-diethanaminium diiodide;

bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosulphate.

14. A method according to claim 1, wherein said acid addition salts of said at least one compound of formula (I) are chosen from hydrochlorides, hydrobromides, sulphates, citrates, succinates, tartrates, lactates and acetates.

15. A composition for dyeing or making up keratin substances, comprising, in an amount effective for dyeing or making up said keratin substances, at least one compound of formula (I) or an acid addition salt thereof:

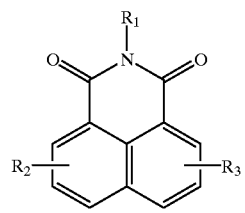

(I)

in which:

R₁ is chosen from a hydrogen atom; a group Z; an amino($C_1$–$C_6$)alkylcarbonyl ($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; an aminosulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-di($C_1$–$C_6$)alkylamino-sulphonyl($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; and a $C_1$–$C_6$ trifluoroalkyl radical;

R₂ and R₃, which are identical or different, are chosen from a hydrogen atom; a halogen atom; a group Z; a ($C_1$–$C_6$)alkylcarbonyl radical; an amino ($C_1$–$C_6$) alkylcarbonyl radical; an N—Z-amino ($C_1$–$C_6$) alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$) alkylcarbonyl radical; an amino ($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$) alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; a carboxyl radical; a ($C_1$–$C_6$) alkylcarboxy radical; a $C_1$–$C_6$ alkylsulphonyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; an aminosulphonyl($C_1$–$C_6$)alkyl radical; an N—Z-aminosulphonyl($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$alkyl radical; a hydroxyl radical; a nitro radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; an amino radical; an N—($C_1$–$C_6$)alkylamino radical; an N,N-di($C_1$–$C_6$) alkylamino radical, wherein the two alkyl substituents optionally form a 5- or 6-membered ring; an N-hydroxy ($C_1$–$C_6$) alkylamino radical; an N,N-bis(hydroxy ($C_1$–$C_6$) alkyl)amino radical; an N-polyhydroxy ($C_2$–$C_6$)alkylamino radical; an N,N-bis(polyhydroxy ($C_2$–$C_6$)alkyl)amino radical; an amino($C_1$–$C_6$) alkylamino radical in which the terminal amino group is unsubstituted or substituted with one or two $C_1$–$C_6$ alkyl radicals, said alkyl radicals optionally forming a saturated or unsaturated 5- or 6-membered ring; an amino group protected with a ($C_1$–$C_6$)alkylcarbonyl, trifluoro($C_1$–$C_6$)alkylcarbonyl, amino($C_1$–$C_6$) alkylcarbonyl, N—Z-amino($C_1$–$C_6$)alkylcarbonyl, N—($C_1$–$C_6$)alkylamino($C_1$–$C_6$)alkyl-carbonyl, N,N-di ($C_1$–$C_6$)alkylamino($C_1$–$C_6$)alkylcarbonyl or formyl radical; and a group OR₄ or SR₄;

R₂ and R₃ alternatively may together form an unsaturated ring of formula (II) below:

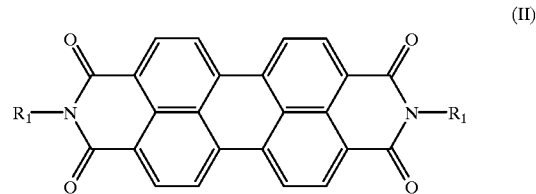

(II)

in which said radical R₁ is chosen from a hydrogen atom; a group Z; an amino($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$) alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; an amino-sulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-di($C_1$–$C_6$)alkylamino-sulphonyl($C_1$–$C_6$) alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; and a $C_1$–$C_6$ trifluoroalkyl radical;

R₄ is chosen from a $C_1$–$C_6$ alkyl radical; a $C_1$–$C_6$ monohydroxyalkyl radical; a $C_2$–$C_6$polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl ($C_1$–$C_6$)alkyl radical; an N—($C_1$–$C_6$) alkyl-carbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonyl-alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; and a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro ($C_1$–$C_6$)alkylcarbonyl, ($C_1$–$C_6$)alkylcarboxyl, and $C_1$–$C_6$ alkylsulphonyl radicals;

Z is chosen from an unsaturated cationic group of formulae (III) or (IV), and a saturated cationic group of formula (V):

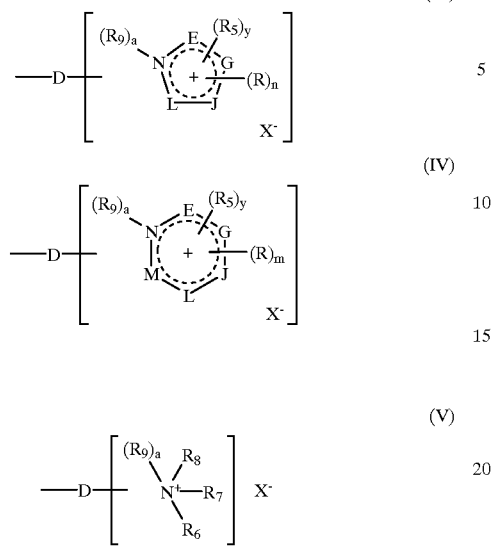

in which:

D is a linker arm chosen from linear and branched alkyl chains, said chains being optionally interrupted by one or more hetero atoms, optionally substituted with one or more hydroxyl or $C_1$–$C_6$ alkoxy radicals, and optionally having one or more ketone functions;

$X^-$ is chosen from monovalent and divalent anions;

said ring members E, G, J, L and M, which are identical or different, are chosen from a carbon, oxygen, sulphur or nitrogen atom;

n is an integer ranging from 0 to 4;

m is an integer ranging from 0 to 5;

said radicals R, which are identical or different, are chosen from a covalent bond, a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano ($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkycarbonyl, carbamyl or $C_1$–$C_6$ alkylsulphonyl radical; and a group NHR" or NR"R"' in which R" and R"', which are identical or different, and are chosen from a $C_1$–$C_6$ alkyl radical, a $C_1$–$C_6$ monohydroxyalkyl radical and a $C_2$–$C_6$ polyhydroxyalkyl radical; when, in formula (III) or (IV), n or m is greater than 2, two adjacent radicals R together optionally form an unsaturated 5- or 6-membered ring which is carbon-based or which contains one or more hetero atoms;

$R_5$ is chosen from a covalent bond, a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane ($C_1$–$C_6$)alkyl radical, a ($C_1$–$C_6$)alkoxy($C_1$–$C_6$)alkyl radical, a carbamyl-($C_1$–$C_6$)alkyl radical, a ($C_1$–$C_6$)alkylcarboxy ($C_1$–$C_6$)alkyl radical, a benzyl radical and a group Z;

$R_6$, $R_7$ and $R_8$, which are identical or different, are chosen from a covalent bond, a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$)alkyl radical, an aryl radical, a benzyl radical, a $C_1$–$C_6$ amidoalkyl radical, a tri($C_1$–$C_6$)alkylsilane($C_1$–$C_6$)alkyl radical and a $C_1$–$C_6$ aminoalkyl radical in which the amine is protected with a ($C_1$–$C_6$)alkylcarbonyl, carbamyl or $C_1$–$C_6$ alkylsulphonyl radical; two of the radicals $R_6$, $R_7$ and $R_8$ together optionally form, with the nitrogen atom to which they are attached, a saturated 5- or 6-membered ring which is carbon-based or contains one or more hetero atoms, one of the radicals $R_6$, $R_7$ and $R_8$ optionally is chosen from a second group Z which is identical to or different from the first group Z;

$R_9$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl($C_1$–$C_6$)alkyl radical; a $C_1$–$C_6$ trifluoroalkyl radical; a tri($C_1$–$C_6$) alkylsilane-($C_1$–$C_6$)alkyl radical; a $C_1$–$C_6$ sulphonamidoalkyl radical; a ($C_1$–$C_6$)alkylcarboxy($C_1$–$C_6$) alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; and an N—($C_1$–$C_6$)alkylsulphonamido($C_1$–$C_6$)alkyl radical;

a and y are integers equal to 0 or 1; with the following provisos:

(A) in the unsaturated cationic groups of formula (III):
  when a=0, the linker arm D is attached to the nitrogen atom,
  when a=1, the linker arm D is attached to one of the ring members E, G, J or L,
  y can take the value 1 only when:
  (1) the ring-members E, G, J and L simultaneously are a carbon atom and when the radical $R_5$ is borne by the nitrogen atom of the unsaturated ring; or
  (2) at least one of the ring members E, G, J and L is a nitrogen atom to which the radical $R_5$ is attached;

(B) in the unsaturated cationic groups of formula (IV):
  when a=0, the linker arm D is attached to the nitrogen atom,
  when a=1, the linker arm D is attached to one of the ring members E, G, J, L or M,
  y can take the value 1 only when at least one of the ring members E, G, J, L and M is a divalent atom and when the radical $R_5$ is borne by the nitrogen atom of the unsaturated ring;

(C) in the cationic groups of formula (V):
  when a=0, then the linker arm D is attached to the nitrogen atom bearing the radicals $R_7$ and $R_8$,
  when a=1, then two of the radicals $R_7$ and $R_8$ form, together with the nitrogen atom to which they are attached, a saturated 5- or 6-membered ring as defined above, and the linker arm D is borne by a carbon atom of the saturated ring;

and with the overall proviso that:
  the number of cationic groups Z of formula (III), (IV) or (V) is at least equal to 1.

16. A composition according to claim 15, wherein said alkyl chain of said linker arm D contains from 1 to 14 carbon atoms.

17. A composition according to claim 15, wherein said one or more heteroatoms optionally interrupting said alkyl chain of said linker arm D are chosen from oxygen, sulfur and nitrogen atoms.

18. A composition according to claim 15, wherein said composition is in a medium suitable for at least one of dyeing and make-up.

19. A composition according to claim 15, wherein said keratin substances are chosen from human skin, lips and nails.

20. A composition according to claim 15, wherein said rings of the unsaturated groups Z of formula (III) are chosen from pyrrole, imidazole, pyrazole, oxazole, thiazole and triazole rings.

21. A composition according to claim 15, wherein said rings of the unsaturated groups Z of formula (IV) are chosen from pyridine, pyrimidine, pyrazine, oxazine and triazine rings.

22. A composition according to claim 15, wherein in said formula (V), two of the radicals $R_6$, $R_7$ and $R_8$ form a pyrrolidine ring, a piperidine ring, a piperazine ring or a morpholine ring, and said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical.

23. A composition according to claim 15, wherein said anion $X^-$ is chosen from a halogen atom, a hydroxide, a hydrogen sulphate and a ($C_1$–$C_6$)alkyl sulphate.

24. A composition according to claim 15, wherein in said formula (I), $R_2$ and $R_3$ together form an unsaturated ring of formula (II).

25. A composition according to claim 15, wherein said compounds of formula (I) are chosen from:
N,N'-dihexyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;
4,4'-{(1,3,8,10-tetrahydro-1,3,8,10-tetraoxoanthra-{2,1,9-def:6,5,10-d'e'f'}diisoquinoline-2,9-diyl)di-3,1-propanediyl}bis{4-methyl}morpholinium diiodide;
N,N,N',N'-tetraethyl-1,3,8,10-tetrahydro-N,N'-dimethyl-1,3,8,10-tetraoxoanthra{2,1,9-def:6,5,10-d'e'f'}diisoquinoline-2,9-dipropanaminium diiodide;
N,N,N',N'-hexaethyl-1,3,8,10-tetrahydro-1,3,8,10-tetraoxoanthra{2,1,9-def:6,5,10-d'e'f'}diisoquinoline-2,9-diethanaminium diiodide;
N,N'-diethyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;
1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;
1,3,8,10-tetrahydro-N,N,N,N',N',N'-hexamethyl-1,3,8,10-tetraoxoanthra{2,1,9-def:6,5,10-d'e'f'}diisoquinoline-2,9-dipropanaminium diiodide;
N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium dibenzenesulphonate;
1,3,8,10-tetrahydro-N,N,N,N',N',N'-hexaethyl-1,3,8,10-tetraoxoanthra{2,1,9-def:6,5,10-d'e'f'}diisoquinoline-2,9-diethanaminium diiodide;
1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium dibenzenesulphonate;
1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;
bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and
bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosulphate.

26. A composition according to claim 25, wherein said compounds of formula (I) are chosen from:
1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;
bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and
bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosulphate.

27. A composition according to claim 15, wherein said acid addition salts of said at least one compound of formula (I) are chosen from hydrochlorides, hydrobromides, sulphates, citrates, succinates, tartrates, lactates and acetates.

28. A composition according to claim 15, having a pH ranging from about 3 to about 12.

29. A direct dye composition for human keratin fibers, comprising in an amount effective for direct dyeing, at least one compound of formula (I) or an acid addition salt thereof:

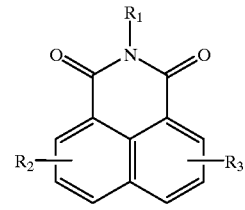

(I)

in which:
$R_1$ is chosen from a hydrogen atom; a group Z; an amino($C_1$–$C_6$)alkylcarbonyl ($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; an aminosulphonyl($C_1$–$C_6$)alkyl radical; an N—Z-aminosulphonyl($C_1$–$C_6$)alkyl radical; an N—($C_1$–$C_6$) alkylaminosulphonyl($C_1$–$C_6$)alkyl radical; an N,N-di ($C_1$–$C_6$)alkylamino sulphonyl($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; and a $C_1$–$C_6$ trifluoroalkyl radical;

$R_2$ and $R_3$, which are identical or different, are chosen from a hydrogen atom; a halogen atom; a group Z; a ($C_1$–$C_6$)alkylcarbonyl radical; an amino ($C_1$–$C_6$) alkylcarbonyl radical; an N—Z-amino($C_1$–$C_6$) alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino ($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$)alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; a carboxyl radical; a ($C_1$–$C_6$) alkylcarboxy radical; a $C_1$–$C_6$ alkylsulphonyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; an aminosulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; an amino radical; an N—($C_1$–$C_6$)alkylamino radical; an N,N-di($C_1$–$C_6$) alkylamino radical, wherein the two alkyl substituents optionally form a 5- or 6-membered ring; an N-hydroxy ($C_1$–$C_6$) alkylamino radical; an N,N-bis(hydroxy ($C_1$–$C_6$) alkyl)amino radical; an N-polyhydroxy ($C_2$–$C_6$)alkylamino radical; an N,N-bis(polyhydroxy ($C_2$–$C_6$)alkyl)amino radical; an amino($C_1$–$C_6$) alkylamino radical in which the terminal amino group is unsubstituted or substituted with one or two $C_1$–$C_6$ alkyl radicals, said alkyl radicals optionally forming a saturated or unsaturated 5- or 6-membered ring; an amino group protected with a ($C_1$–$C_6$)alkylcarbonyl, trifluoro($C_1$–$C_6$)alkylcarbonyl, amino($C_1$–$C_6$) alkylcarbonyl, N—Z-amino($C_1$–$C_6$)alkylcarbonyl, N—($C_1$–$C_6$)alkylamino($C_1$–$C_6$)alkyl-carbonyl, N,N-di ($C_1$–$C_6$)alkylamino($C_1$–$C_6$)alkylcarbonyl or formyl radical; and a group $OR_4$ or $SR_4$;

$R_2$ and $R_3$ alternatively may together form an unsaturated ring of formula (II) below:

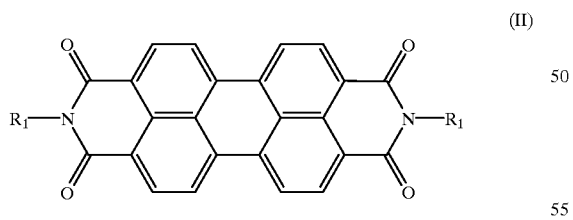

(II)

in which said radical $R_1$ is chosen from a hydrogen atom; a group Z; an amino($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$) alkylamino($C_1$–$C_6$)alkylcarbonyl($C_1$–$C_6$)alkyl radical; an N,N-di($C_1$–$C_6$)alkylamino($C_1$–$C_6$)alkylcarbonyl ($C_1$–$C_6$)alkyl radical; an amino-sulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-di($C_1$–$C_6$)alkylamino-sulphonyl($C_1$–$C_6$) alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; and a $C_1$–$C_6$ trifluoroalkyl radical;

$R_4$ is chosen from a $C_1$–$C_6$ alkyl radical; a $C_1$–$C_6$ monohydroxyalkyl radical; a $C_2$–$C_6$ polyhydroxy alkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl ($C_1$–$C_6$) alkyl radical; an N—($C_1$–$C_6$) alkyl-carbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonyl-alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; and a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro ($C_1$–$C_6$)alkylcarbonyl, ($C_1$–$C_6$)alkylcarboxyl, and $C_1$–$C_6$ alkylsulphonyl radicals;

Z is chosen from an unsaturated cationic group of formulae (III) or (IV), and a saturated cationic group of formula (V):

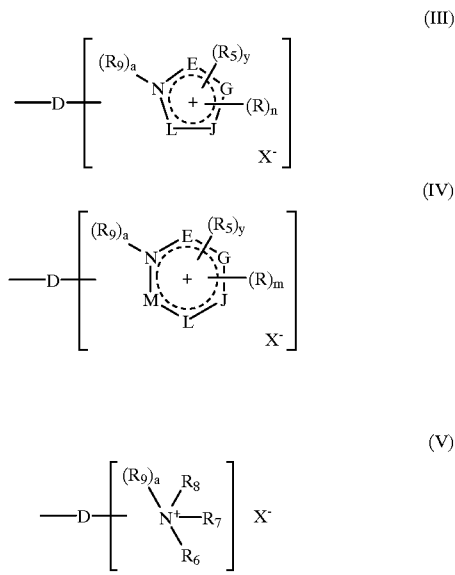

in which:

D is a linker arm chosen from linear and branched alkyl chains, said chains being optionally interrupted by one or more hetero atoms, optionally substituted with one or more hydroxyl or $C_1$–$C_6$ alkoxy radicals, and optionally having one or more ketone functions;

$X^-$ is chosen from monovalent and divalent anions;

said ring members E, G, J, L and M, which are identical or different, are chosen from a carbon, oxygen, sulphur or nitrogen atom;

n is an integer ranging from 0 to 4;

m is an integer ranging from 0 to 5;
said radicals R, which are identical or different, are chosen from a covalent bond, a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; and a group NHR" or NR"R'" in which R" and R'", which are identical or different, and are chosen from a $C_1$–$C_6$ alkyl radical, a $C_1$–$C_6$ monohydroxyalkyl radical and a $C_2$–$C_6$ polyhydroxyalkyl radical; when, in formula (III) or (IV), n or m is greater than 2, two adjacent radicals R together optionally form an unsaturated 5- or 6-membered ring which is carbon-based or which contains one or more hetero atoms;
$R_5$ is chosen from a covalent bond, a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane ($C_1$–$C_6$)alkyl radical, a ($C_1$–$C_6$)alkoxy($C_1$–$C_6$)alkyl radical, a carbamyl-($C_1$–$C_6$)alkyl radical, a ($C_1$–$C_6$)alkylcarboxy ($C_1$–$C_6$)alkyl radical, a benzyl radical and a group Z;
$R_6$, $R_7$ and $R_8$, which are identical or different, are chosen from a covalent bond, a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$)alkyl radical, an aryl radical, a benzyl radical, a $C_1$–$C_6$ amidoalkyl radical, a tri($C_1$–$C_6$)alkylsilane($C_1$–$C_6$)alkyl radical and a $C_1$–$C_6$ aminoalkyl radical in which the amine is protected with a ($C_1$–$C_6$)alkylcarbonyl, carbamyl or $C_1$–$C_6$ alkylsulphonyl radical; two of the radicals $R_6$, $R_7$ and $R_8$ together optionally form, with the nitrogen atom to which they are attached, a saturated 5- or 6-membered ring which is carbon-based or contains one or more hetero atoms, one of the radicals $R_6$, $R_7$ and $R_8$ optionally is chosen from a second group Z which is identical to or different from the first group Z;
$R_9$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano ($C_1$–$C_6$)alkyl radical; a carbamyl($C_1$–$C_6$)alkyl radical; a $C_1$–$C_6$ trifluoroalkyl radical; a tri($C_1$–$C_6$) alkylsilane-($C_1$–$C_6$)alkyl radical; a $C_1$–$C_6$ sulphonamidoalkyl radical; a ($C_1$–$C_6$)alkylcarboxy($C_1$–$C_6$) alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; and an N—($C_1$–$C_6$)alkylsulphonamido($C_1$–$C_6$)alkyl radical;
a and y are integers equal to 0 or 1; with the following provisos:
(A) in the unsaturated cationic groups of formula (III):
when a=0, the linker arm D is attached to the nitrogen atom,
when a=1, the linker arm D is attached to one of the ring members E, G, J or L,
y can take the value 1 only when:
(1) the ring-members E, G, J and L simultaneously are a carbon atom and when the radical $R_5$ is borne by the nitrogen atom of the unsaturated ring; or
(2) at least one of the ring members E, G, J and L is a nitrogen atom to which the radical $R_5$ is attached;
(B) in the unsaturated cationic groups of formula (IV):
when a=0, the linker arm D is attached to the nitrogen atom,
when a=1, the linker arm D is attached to one of the ring members E, G, J, L or M,
y can take the value 1 only when at least one of the ring members E, G, J, L and M is a divalent atom and when the radical $R_5$ is borne by the nitrogen atom of the unsaturated ring;
(C) in the cationic groups of formula (V):
when a=0, then the linker arm D is attached to the nitrogen atom bearing the radicals $R_7$ and $R_8$,
when a=1, then two of the radicals $R_7$ and $R_8$ form, together with the nitrogen atom to which they are attached, a saturated 5- or 6-membered ring as defined above, and the linker arm D is borne by a carbon atom of the saturated ring;
and with the overall proviso that:
the number of cationic groups Z of formula (III), (IV) or (V) is at least equal to 1.

30. A composition according to claim 29, wherein said alkyl chain of said linker arm D contains from 1 to 14 carbon atoms.

31. A composition according to claim 29, wherein said one or more heteroatoms optionally interrupting said alkyl chain of said linker arm D are chosen from oxygen, sulfur and nitrogen atoms.

32. A composition according to claim 29, wherein said composition is in a medium suitable for dyeing.

33. A composition according to claim 29, wherein said human keratin fibers are human hair.

34. A composition according to claim 29, wherein said rings of the unsaturated groups Z of formula (III) are chosen from pyrrole, imidazole, pyrazole, oxazole, thiazole and triazole rings.

35. A composition according to claim 29, wherein said rings of the unsaturated groups Z of formula (IV) are chosen from pyridine, pyrimidine, pyrazine, oxazine and triazine rings.

36. A composition according to claim 29, wherein in said formula (V), two of the radicals $R_6$, $R_7$ and $R_8$ form a pyrrolidine ring, a piperidine ring, a piperazine ring or a morpholine ring, and said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri ($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical.

37. A composition according to claim 29, wherein said anion $X^-$ is chosen from a halogen atom, a hydroxide, a hydrogen sulphate and a ($C_1$–$C_6$)alkyl sulphate.

38. A composition according to claim 29, wherein in said formula (I), $R_2$ and $R_3$ together form an unsaturated ring of formula (II).

39. A composition according to claim 29, wherein said compounds of formula (I) are chosen from:

N,N'-dihexyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;

4,4'-{(1,3,8,10-tetrahydro-1,3,8,10-tetraoxoanthra-{2,1,9-def:6,5,10-d'e'f'}diisoquinoline-2,9-diyl)di-3,1-propanediyl}bis{4-methyl}morpholinium diiodide;

N,N,N',N'-tetraethyl-1,3,8,10-tetrahydro-N,N'-dimethyl-1,3,8,10-tetraoxoanthra{2,1,9-def:6,5,10-d'e'f'}diisoquinoline-2,9-dipropanaminium diiodide;

N,N,N ,N',N',N'-hexaethyl-1,3,8,10-tetrahydro-1,3,8,10-tetraoxoanthra{2,1,9-def:6,5,10-d'e'f'}diisoquinoline-2,9-diethanaminium diiodide;

N,N'-diethyl-1,3,8,10-tetrahydro-N,N,N',N'-tetramethyl-1,3,8,10-tetraoxoanthra{2,1,9-def:6,5,10-d'e'f'}diisoquinoline-2,9-dipropanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-dipropanaminium diiodide;

N,N,N,N',N',N'-hexaethyl-1,3,8,10-tetrahydro-1,3,8,10-tetraoxoanthra{2,1,9-def:6,5,10-d'e'f'}diisoquinoline-2,9-diethanaminium dibenzenesulphonate;

1,3,8,10-tetrahydro-N,N,N,N',N',N'-hexaethyl-1,3,8,10-tetraoxoanthra{2,1,9-def:6,5,10-d'e'f'}diisoquinoline-2,9-diethanaminium diiodide;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium dibenzenesulphonate;

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

bis{-1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosulphate.

40. A composition according to claim 39, wherein said compounds of formula (I) are chosen from:

1,3,8,10-tetrahydro-N,N,N,N',N',N'-hexamethyl-1,3,8,10-tetraoxoanthra{2,1,9-def:6,5,10-d'e'f'}diisoquinoline-2,9-diethanaminium diiodide;

bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium diiodide; and bis{1-1'-methyl}-1,1'-{(1,3,8,10-tetrahydro-1,3,8,10-tetraoxoanthra{2,1,9-def:6,5,10-d'e'f'}diisoquinoline-2,9-diyl)di-3,1-propanediyl}imidazolinium dimethosuiphate.

41. A composition according to claim 29, wherein said acid addition salts of said at least one compound of formula (I) are chosen from hydrochlorides, hydrobromides, sulphates, citrates, succinates, tartrates, lactates and acetates thereof.

42. A composition according to claim 29, having a pH ranging from about 3 to about 12.

43. A dye composition according to claim 29, wherein said at least one compound of formula (I) is present in an amount ranging from 0.005 to 12% by weight relative to the total weight of the composition.

44. A composition according to claim 43, wherein said at least one compound of formula (I) is present in an amount ranging from 0.05 to 6% by weight relative to the total weight of the composition.

45. A composition according to claim 32, wherein said medium suitable for dyeing is an aqueous medium comprising water or a mixture of water and at least one organic solvent, wherein said at least one organic solvent is present in an amount ranging from 1 to 40% by weight relative to the total weight of the composition.

46. A composition according to claim 18, wherein said medium suitable for at least one of dyeing and make-up is an aqueous medium comprising water or a mixture of water and at least one organic solvent, wherein said at least one organic solvent is present in an amount ranging from 1 to 40% by weight relative to the total weight of the composition.

47. A make-up composition according to claim 15, wherein said at least one compound of formula (I) is present in an amount ranging from 0.005 to 25% by weight relative to the total weight of the composition.

48. A composition according to claim 15, wherein said composition is in the form of a make-up product for human skin, lips, nails, eyelashes or eyebrows.

49. A composition according to claim 48, wherein said composition is in the form of a foundation, a face powder, an eyeshadow, a rouge, a blusher, a lipstick, a lip gloss, a nail varnish, a mascara or an eyeliner.

50. A method for dyeing keratin fibers according to claim 1, wherein said direct dye composition is applied to wet or dry keratin fibers, and wherein said keratin fibers are dried without intermediate rinsing.

51. A method according to claim 50, wherein said keratin fibers are human hair.

52. A method for dyeing keratin fibers according to claim 1, further comprising applying said direct dye composition to wet or dry keratin fibers, optionally leaving said dye composition on said keratin fibers for 3 to 60 minutes, rinsing said keratin fibers, optionally washing and rinsing said keratin fibers, and drying said keratin fibers.

53. A method according to claim 52, wherein said keratin fibers are human hair.

* * * * *

UNITED STATES PATENT AND TRADEMARK OFFICE
CERTIFICATE OF CORRECTION

PATENT NO. : 6,391,062 B1
DATED : May 21, 2002
INVENTOR(S) : Jean Jacques Vandenbossche et al.

It is certified that error appears in the above-identified patent and that said Letters Patent is hereby corrected as shown below:

Column 12,
Line 18, "$C_1$-$C_6$alkyl" should read -- $C_1$-$C_6$ alkyl --.
Line 55, "alkyl carbonyl" should read -- alkylcarbonyl --.

Column 13,
Line 3, after "alkyl", insert -- radical --.

Column 14,
Line 40, "$C_1$ -$C_6$" should read -- $C_1$-$C_6$ --.

Column 16,
Line 12, "diisoquinoine" should read -- diisoquinoline --.
Line 30, "1,3,8,10tetrahydro", should read -- 1,3,8,10-tetrahydro --.
Lines 30 and 31, "1,3,8,10tetraoxoanthra" should read -- 1,3,8,10-tetraoxoanthra --.
Line 50, "N,N,N,N',N', N' " should read -- N,N,N,N',N',N' --.

Column 17,
Line 54, "$C_1$ -$C_6$alkyl" should read -- $C_1$-$C_6$alkyl --.

Column 18,
Line 36, "$C_1$ -$C_6$alkyl" should read -- $C_1$-$C_6$alkyl --.
Line 41, "$C_2$ -$C_6$polyhydroxyalkyl" should read -- $C_2$-$C_6$ polyhydroxyalkyl --.

Column 21,
Line 59, "N,N,N ,N',N',N' " should read -- N,N,N,N',N',N' --.

Column 22,
Lines 12 and 15, "di-3,1 -propanediyl" should read -- di-3,1-propanediyl --.
Line 59, "alkylamino sulphonyl", should read -- alkylaminosulphonyl. --

Column 23,
Line 63, "amino-sulphonyl" should read -- aminosulphonyl --.

Column 24,
Line 8, "polyhydroxy alkyl" should read -- polyhydroxyalkyl --.

UNITED STATES PATENT AND TRADEMARK OFFICE
CERTIFICATE OF CORRECTION

PATENT NO. : 6,391,062 B1
DATED : May 21, 2002
INVENTOR(S) : Jean Jacques Vandenbossche et al.

It is certified that error appears in the above-identified patent and that said Letters Patent is hereby corrected as shown below:

<u>Column 27,</u>
Line 15, "N,N,N ,N',N',N' " should read -- N,N,N,N',N',N' --.
Line 39, "{-1-1'-methyl}" should read -- {1-1'-methyl} --.
Lines 44 and 52, "di-3,1 –propanediyl" should read -- di-3,1-propanediyl --.
Line 55, "dimethosuiphate" should read -- dimethosulphate --.

Signed and Sealed this

Sixth Day of August, 2002

*Attest:*

*Attesting Officer*

JAMES E. ROGAN
*Director of the United States Patent and Trademark Office*